(12) United States Patent
Takada

(10) Patent No.: US 10,034,602 B2
(45) Date of Patent: Jul. 31, 2018

(54) FLUID FEEDING APPARATUS AND ENDOSCOPE REPROCESSOR

(71) Applicant: OLYMPUS CORPORATION, Tokyo (JP)

(72) Inventor: Hiroo Takada, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/646,167

(22) Filed: Jul. 11, 2017

(65) Prior Publication Data

US 2017/0303777 A1    Oct. 26, 2017

Related U.S. Application Data

(63) Continuation of application No. PCT/JP2016/083426, filed on Nov. 10, 2016.

(30) Foreign Application Priority Data

Feb. 3, 2016    (JP) .................................. 2016-019001

(51) Int. Cl.
| | |
|---|---|
| A61B 1/12 | (2006.01) |
| B08B 9/032 | (2006.01) |
| B08B 9/023 | (2006.01) |
| A61L 2/18 | (2006.01) |
| F16K 1/20 | (2006.01) |
| F16K 7/04 | (2006.01) |

(52) U.S. Cl.
CPC .............. *A61B 1/123* (2013.01); *A61B 1/125* (2013.01); *A61L 2/18* (2013.01); *B08B 9/023* (2013.01); *B08B 9/0321* (2013.01); *A61L 2202/17* (2013.01); *A61L 2202/24* (2013.01); *F16K 1/20* (2013.01); *F16K 7/04* (2013.01)

(58) Field of Classification Search
CPC ..................................................... A61B 1/123
See application file for complete search history.

(56) References Cited

FOREIGN PATENT DOCUMENTS

| | | |
|---|---|---|
| JP | S60-120998 U1 | 8/1985 |
| JP | 2006-314709 A | 11/2006 |
| JP | 2010-035620 A | 2/2010 |

*Primary Examiner* — Jason Y Ko

(74) *Attorney, Agent, or Firm* — Scully, Scott, Murphy & Presser, P.C.

(57) ABSTRACT

A fluid feeding apparatus includes: a first connection portion configured to be connected to a first container in which fluid is stored; a second connection portion configured to be connected to a second container in which fluid is stored; a first flow path that communicates with the first connection portion; a second flow path that communicates with the second connection portion; a resistance portion configured to generate a difference of conduit resistance to cause one of the first flow path and the second flow path to be higher in the conduit resistance than the other flow path; and a switching portion switching a level relationship of the conduit resistance between the first flow path and the second flow path.

3 Claims, 6 Drawing Sheets

| N | A | B |
|---|---|---|
| 0 | 20 | 20 |
| 1 | 17 | 19 |
| 2 | 14 | 18 |
| 3 | 11 | 17 |
| 4 | 8 | 16 |
| 5 | 5 | 15 |
| 6 | 2 | 14 |
| 7 | 0 | 12 |
| 8 | 0 | 8 |
| 9 | 0 | 4 |
| 10 | 0 | 0 |

FIG. 6

| N | A | B |
|---|---|---|
| 9 | 20 | 4 |
| 10 | 19 | 1 |
| 11 | 16 | 0 |
| 12 | 12 | 0 |
| 13 | 8 | 0 |
| 14 | 4 | 0 |
| 15 | 0 | 0 |

FIG. 7

| N | A | B |
|---|---|---|
| 13 | 8 | 20 |
| 14 | 5 | 19 |
| 15 | 2 | 18 |
| 16 | 0 | 16 |
| 17 | 0 | 12 |
| 18 | 0 | 8 |
| 19 | 0 | 4 |
| 20 | 0 | 4 |

FLUID FEEDING APPARATUS AND ENDOSCOPE REPROCESSOR

CROSS REFERENCE TO RELATED APPLICATION

This application is a continuation application of PCT/JP2016/083426 filed on Nov. 10, 2016 and claims benefit of Japanese Application No. 2016-019001 filed in Japan on Feb. 3, 2016, the entire contents of which are incorporated herein by this reference.

BACKGROUND OF THE INVENTION

1. Field of the Invention

The present invention relates to a fluid feeding apparatus that feeds fluid stored in a container, and to an endoscope reprocessor.

2. Description of the Related Art

An endoscope used in a medical field is subjected to reprocessing such as cleaning treatment and disinfection treatment after use. In addition, an endoscope reprocessor that automatically performs the reprocessing of the endoscope is well-known as disclosed in, for example, Japanese Patent Application Laid-Open Publication No. 2006-314709. The reprocessing is performed through introduction of a predetermined volume of fluid such as a medicinal solution and tap water into a treatment tank in which the endoscope is placed.

For example, the endoscope reprocessor disclosed in Japanese Patent Application Laid-Open Publication No. 2006-314709, includes a cleaning agent tank in which a cleaning agent is stored, and a flow rate sensor that detects a flow rate of the cleaning agent supplied from the cleaning agent tank into the treatment tank, and supplies a predetermined volume of the cleaning agent into the treatment tank. The endoscope reprocessor disclosed in Japanese Patent Application Laid-Open Publication No. 2006-314709 gives a user a warning that the cleaning agent has run out, thereby prompting the user to add the cleaning agent when the reprocessing is repeatedly executed and the cleaning agent in the cleaning agent tank has been entirely consumed.

SUMMARY OF THE INVENTION

A fluid feeding apparatus according to an aspect of the present invention includes: a first connection portion configured to be connected to a first container in which fluid is stored; a second connection portion configured to be connected to a second container in which fluid is stored; a first flow path that communicates with the first connection portion; a second flow path that communicates with the second connection portion; a confluent part at which the first flow path and the second flow path are joined; a suction portion connected to the confluent part, the suction portion being configured to suck the fluid from the first connection portion and the second connection portion at the same time to feed the fluid from a feed part; a resistance portion configured to generate a difference of conduit resistance to cause one of the first flow path and the second flow path to be higher in the conduit resistance than the other flow path and to cause a flow rate of each of the first flow path and the second flow path to exceed zero during operation of the suction portion; and a switching portion connected to the resistance portion, the switching portion switching a level relationship of the conduit resistance between the first flow path and the second flow path, in which the resistance portion includes a valve part having a flow rate that exceeds zero, and the switching portion movably supports the valve part between a position at which the valve part extends into the first flow path and a position at which the valve part extends into the second flow path.

In addition, an endoscope reprocessor according to an aspect of the present invention includes: a treatment tank in which an endoscope is disposed; and the fluid feeding apparatus, in which the first flow path and the second flow path are connected to the treatment tank through the suction portion.

DETAILED DESCRIPTION OF THE PREFERRED EMBODIMENT

A preferred embodiment of the present invention is described below with reference to drawings. Note that, in the drawings used for the following description, scale size is varied for each component in order to illustrate each component with a recognizable size in the drawings. The present invention is not limited to only the number of components, shapes of respective components, a size ratio of components, and relative positional relationship between components illustrated in the drawings.

An example of the embodiment of the present invention is described below. An endoscope reprocessor 1 illustrated in FIG. 1 performs reprocessing on an endoscope. The reprocessing used herein is not particularly limited, and may indicate rinsing treatment with water, cleaning treatment to wash out a stain such as organic matters, disinfection treatment to neutralize predetermined microorganisms, sterilization treatment to eliminate or annihilate all microorganisms, or a combination of the treatments.

Note that, in the following description, upper side indicates a position far away from the ground with respect to a comparative target, and lower side indicates a position closer to the ground with respect to the comparative target. In addition, level in the following description indicates a height relationship along the gravity direction.

Figure 1:
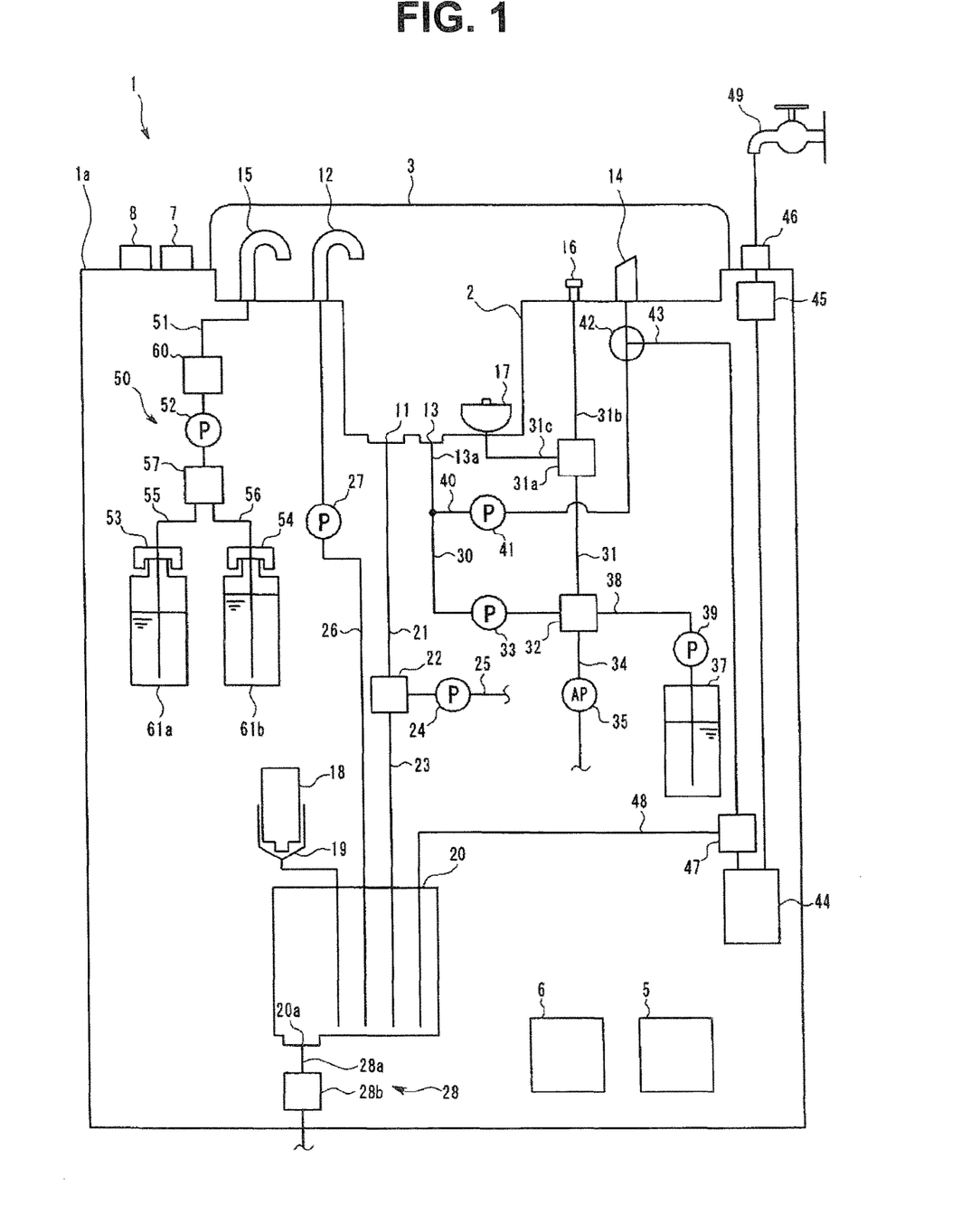
FIG. 1 is a diagram illustrating a configuration of an endoscope reprocessor including a fluid feeding apparatus.

The endoscope reprocessor 1 includes a control section 5, a power supply section 6, a treatment tank 2, and a fluid feeding apparatus 50.

The control section 5 is configured to include a calculation device (CPU), a memory device (RAM), an auxiliary memory device, an input-output device, a power control device, and the like. The control section 5 controls operation of each of the parts configuring the endoscope reprocessor 1, on the basis of predetermined programs. Operation of each of the parts included in the endoscope reprocessor 1 in the following description is controlled by the control section 5 even though particular description is not given.

The power supply section 6 supplies power to the parts of the endoscope reprocessor 1. The power supply section 6 distributes power provided from outside such as a commercial power supply, to the respective parts. Note that the power supply section 6 may include one of a power generator and a buttery.

An operation section 7 and a display section 8 configure a user interface through which information is transferred to/from a user. The operation section 7 includes an operation member that receives operation instruction from the user, such as a push switch and a touch sensor. The operation instruction from the user is converted into an electric signal by the operation section 7, and the electric signal is provided to the control section 5. The operation instruction from the user indicates, for example, start instruction of the reprocessing. Note that the operation section 7 may be provided in an electronic apparatus separated from a main body 1a of the endoscope reprocessor 1. The electronic apparatus performs one of wired communication and wireless communication with the control section 5.

Moreover, the display section 8 includes, for example, a display device that displays an image and a character, a light emitting device that emits light, a speaker that emits a sound, a vibrator that generates vibration, or a combination of the devices. The display section 8 provides the information from the control section 5 to the user. Note that the display section 8 may be provided in the electronic apparatus separated from the main body 1a of the endoscope reprocessor 1. The electronic apparatus performs one of wired communication and wireless communication with the control section 5.

The treatment tank 2 is formed in a concave shape including an opening part, and liquid is stored inside the treatment tank 2. An unillustrated endoscope may be disposed inside the treatment tank 2. A plurality of endoscopes may be disposed inside the treatment tank 2.

A lid 3 to open or close the opening part of the treatment tank 2 is provided at an upper part of the treatment tank 2. When the reprocessing is performed on the endoscope inside the treatment tank 2, the opening part of the treatment tank 2 is closed by the lid 3.

The treatment tank 2 includes a fluid nozzle 15, a disinfectant nozzle 12, a liquid discharge port 11, a circulation port 13, a circulation nozzle 14, an endoscope connection portion 16, and an accessary case 17.

The fluid nozzle 15 communicates with a feed part 51 of the fluid feeding apparatus 50 described later. The fluid feeding apparatus 50 is schematically connectable to a first container 61a and a second container 61b that are paired containers in which liquid fluid is stored. The fluid stored in the first container 61a and the second container 61b is fed from the feed part 51. The fluid fed from the feed part 51 is introduced into the treatment tank 2 through the fluid nozzle 15.

Note that the first container 61a and the second container 61b are distinguished by different names and different reference numerals in order to describe the present invention, and the different names and the different reference numerals do not intend to imply that different kinds of liquid are stored in the first container 61a and the second container 61b. The first container 61a and the second container 61b may have the same shape or different shapes.

The same kind of liquid is stored in the first container 61a and the second container 61b. A storage amount of the liquid in the first container 61a may be preferably equal to a storage amount of the liquid in the second container 61b. This allows for replacement of the first container 61a and the second container 61b with each other. In the present embodiment, a container connected to a first connection portion 53 described later of the fluid feeding apparatus 50 is referred to as the first container 61a, and a container connected to a second connection portion 54 described later of the fluid feeding apparatus 50 is referred to as the second container 61b. In other words, the paired containers in a state of being not connected to the first connection portion 53 or the second connection portion 54 have no difference.

In the present embodiment, as an example, a container connected to the fluid feeding apparatus 50 is provided in a state where a predetermined amount of liquid is sealed in the container, from a manufacturer of the liquid. When all of the liquid in the container is lost by execution of the reprocessing of the endoscope reprocessor 1, the user of the endoscope reprocessor 1 replaces the used empty container with an unused container.

Note that each of the first container 61a and the second container 61b is illustrated as a bottle container with a fixed shape in FIG. 1; however, each of the first container 61a and the second container 61b may have a deformable bag-like or bellows-like shape.

The fluid stored in the first container 61a and the second container 61b is used for the reprocessing of the endoscope, and the kind of the fluid is not particularly limited. In the present embodiment, as an example, the fluid is a cleaning liquid used for the cleaning treatment. Note that the fluid stored in the first container 61a and the second container 61b may be, for example, a disinfectant used for the disinfection treatment, a sterile liquid used for the sterilization treatment, a medicinal solution such as a highly volatile solution used for drying, or distilled water.

The disinfectant nozzle 12 is an opening part communicating with a disinfectant tank 20 through a disinfectant conduit 26. The disinfectant used for the disinfection treatment is stored in the disinfectant tank 20. The disinfectant conduit 26 includes a disinfectant pump 27. Operation of the disinfectant pump 27 causes the disinfectant in the disinfectant tank 20 to be transferred into the treatment tank 2 through the disinfectant conduit 26 and the disinfectant nozzle 12. The disinfectant pump 27 is connected to the control section 5, and the operation of the disinfectant pump 27 is controlled by the control section 5.

Moreover, in the present embodiment, as an example, the disinfectant is obtained by diluting an original liquid of the disinfectant supplied from a disinfectant bottle 18 with water at a predetermined ratio. The disinfectant tank 20 of the present embodiment communicates with a bottle connection portion 19 that introduces, into the disinfectant tank 20, the original liquid of the disinfectant supplied from the disinfectant bottle 18. The disinfectant bottle 18 is connected to the bottle connection portion 19 to introduce the original liquid of the disinfectant into the disinfectant tank 20. The endoscope reprocessor 1 according to the present invention may include a dilution conduit 48 that introduces dilution water into the disinfectant tank 20. A configuration in which water is introduced from the dilution conduit 48 into the disinfectant tank 20 is described later.

Note that the endoscope reprocessor 1 may not include the configuration in which the disinfectant is diluted with water or the like. Moreover, when the disinfectant is a combination of a plurality of kinds of original liquids, the bottle connection portion 19 is connectable to the plurality of disinfectant bottles 18.

Further, in the present embodiment, as an example, the disinfectant is reusable when the disinfectant has concentration within a predetermined effective range. The disinfectant tank 20 also functions as a disinfectant recovery section that recovers the disinfectant transferred from the disinfectant tank 20 into the treatment tank 2 and stores the recovered disinfectant again.

In addition, the disinfectant tank 20 includes a liquid discharge portion 28. The liquid discharge portion 28 discharges liquid such as the disinfectant and water from the disinfectant tank 20. The liquid discharge portion 28 may discharge the liquid from the disinfectant tank 20 by the gravity, or may forcibly discharge the liquid from the disinfectant tank 20 with use of a pump.

In the present embodiment, as an example, the liquid discharge portion 28 includes a drain conduit 28a and a drain valve 28b. The drain conduit 28a communicates with a liquid discharge port 20a that is provided on or near a bottom surface of the disinfectant tank 20. The drain valve 28b opens or closes the drain conduit 28a. The drain valve 28b may be a solenoid valve that is opened or closed by the control section 5, or a cock that is opened or closed through manual operation of the user.

Note that a path through which the liquid is discharged from the disinfectant tank 20 is not limited only to the drain conduit 28a. For example, starting the operation of the disinfectant pump 27 makes it possible to discharge the liquid from the disinfectant tank 20 into the treatment tank 2 through the disinfectant conduit 26 and the disinfectant nozzle 12. In this case, the endoscope reprocessor 1 may not include the liquid discharge port 20a, the drain conduit 28a, and the drain valve 28b that are illustrated in FIG. 1.

The liquid discharge port 11 is an opening part that is provided at a lowermost position inside the treatment tank 2. The liquid discharge port 11 is connected to a discharge conduit 21. The discharge conduit 21 causes the liquid discharge port 11 and a switching valve 22 to communicate with each other. The switching valve 22 is connected to a recovery conduit 23 and a waste conduit 25. The switching valve 22 is switchable to a state of blocking the discharge conduit 21, a state of causing the discharge conduit 21 and the recovery conduit 23 to communicate with each other, or a state of causing the discharge conduit 21 and the waste conduit 25 to communicate with each other. The switching valve 22 is connected to the control section 5, and operation of the switching valve 22 is controlled by the control section 5.

The recovery conduit 23 causes the disinfectant tank 20 and the switching valve 22 to communicate with each other. In addition, the waste conduit 25 includes a discharge pump 24. The discharge pump 24 is connected to the control section 5, and operation of the discharge pump 24 is controlled by the control section 5. The waste conduit 25 is connected to liquid discharge equipment that receives the liquid discharged from the endoscope reprocessor 1.

Closing the switching valve 22 makes it possible to store the liquid in the treatment tank 2. In addition, when the switching valve 22 is switched to the state of causing the discharge conduit 21 and the recovery conduit 23 to communicate with each other while the disinfectant is stored in the treatment tank 2, the disinfectant is transferred from the treatment tank 2 to the disinfectant tank 20. In addition, when the switching valve 22 is switched to the state of causing the discharge conduit 21 and the waste conduit 25 to communicate with each other and operation of the discharge pump 24 is started, the liquid in the treatment tank 2 is transferred to the liquid discharge equipment through the waste conduit 25.

The circulation port 13 is an opening part provided near the bottom surface of the treatment tank 2. The circulation port 13 communicates with a circulation conduit 13a. The circulation conduit 13a is branched into two conduits of an endoscope circulation conduit 30 and a treatment tank circulation conduit 40.

The endoscope circulation conduit 30 causes the circulation conduit 13a and a channel block 32 described later to communicate with each other. The endoscope circulation conduit 30 includes a circulation pump 33. The circulation pump 33 is operated to transfer the fluid inside the endoscope circulation conduit 30 toward the channel block 32.

The channel block 32 is connected to an intake conduit 34, an alcohol conduit 38, and a feed conduit 31, in addition to the above-described endoscope circulation conduit 30. The channel block 32 connects the feed conduit 31 to the endoscope circulation conduit 30, the intake conduit 34, and the alcohol conduit 38. The channel block 32 includes a check valve that allows flow of the fluid only in a direction from each of the endoscope circulation conduit 30, the intake conduit 34, and the alcohol conduit 38 toward the inside of the channel block 32. In other words, the fluid is prevented from flowing from the inside of the channel block 32 toward the endoscope circulation conduit 30, the intake conduit 34, and the alcohol conduit 38.

The intake conduit 34 has one end part that is opened to the atmosphere and the other end that is connected to the channel block 32. Note that, although not illustrated, the one end part of the intake conduit 34 is provided with a filter that filters passing gas. An air pump 35 is provided in the intake conduit 34, and is operated to transfer the gas inside the intake conduit 34 toward the channel block 32.

The alcohol conduit 38 causes an alcohol tank 37 and the channel block 32 to communicate with each other. Alcohol is stored in the alcohol tank 37. Examples of the alcohol stored in the alcohol tank 37 include ethanol. Alcohol concentration is optionally selected. An alcohol pump 39 is provided in the alcohol conduit 38, and is operated to transfer the alcohol inside the alcohol tank 37 toward the channel block 32.

The circulation pump 33, the air pump 35, and the alcohol pump 39 are connected to the control section 5, and operation of the pumps are controlled by the control section 5. When the operation of the circulation pump 33 is started while the liquid is stored in the treatment tank 2, the liquid in the treatment tank 2 is supplied into the feed conduit 31 through the circulation port 13, the circulation conduit 13a, and the endoscope circulation conduit 30. In addition, when operation of the air pump 35 is started, the air is supplied into the feed conduit 31. Further, when operation of the alcohol pump 39 is started, the alcohol in the alcohol tank 37 is supplied into the feed conduit 31.

The feed conduit 31 is branched into an endoscope connection conduit 31b and a case connection conduit 31c. The endoscope connection conduit 31b is connected to the endoscope connection portion 16. In addition, the case connection conduit 31c is connected to the accessary case 17.

Moreover, the feed conduit 31 includes a flow path switching portion 31a. The flow path switching portion 31a is a relief valve that constantly connects the feed conduit 31 to the endoscope connection conduit 31b. When pressure inside the endoscope connection conduit 31b exceeds a predetermined value, the flow path switching portion 31a releases the fluid flown from the feed conduit 31, to the case connection conduit 31c. In other words, the flow path switching portion 31a maintains constant pressure inside the endoscope connection conduit 31b.

The endoscope connection portion 16 is connected to a pipe sleeve provided on the endoscope. The endoscope connection portion 16 may be directly connected to the pipe sleeve, or may be connected to the pipe sleeve through a connection tube. The accessary case 17 is a basket-like member that contains unillustrated accessories of the endoscope.

The fluid fed from the channel block 32 to the feed conduit 31 is introduced into a conduit that communicates with the pipe sleeve of the endoscope, through the endoscope connection portion 16 and a cleaning tube. When pressure of the fluid introduced into the conduit exceeds a value that operates the flow path switching portion 31a serving as the relief valve, the fluid is also introduced into the accessary case 17 through the case connection conduit 31c, in addition to the conduit of the endoscope.

The treatment tank circulation conduit 40 causes the circulation conduit 13a and the circulation nozzle 14 to communicate with each other. The circulation nozzle 14 is an opening part provided inside the treatment tank 2. The treatment tank circulation conduit 40 includes a liquid flow pump 41. The liquid flow pump 41 is connected to the control section 5, and operation of the liquid flow pump 41 is controlled by the control section 5.

In addition, a three-way valve 42 is provided in the treatment tank circulation conduit 40 between the liquid flow pump 41 and the circulation nozzle 14. The three-way valve 42 is connected to a water supply conduit 43. The three-way valve 42 is switchable to a state of causing the circulation nozzle 14 and the treatment tank circulation conduit 40 to communicate with each other or a state of causing the circulation nozzle 14 and the water supply conduit 43 to communicate with each other.

The water supply conduit 43 causes the three-way valve 42 and a water supply source connection portion 46 to communicate with each other. The water supply conduit 43 includes a water introduction valve 45 and a water filter 44. The water introduction valve 45 opens or closes the water supply conduit 43. The water filter 44 filters water. The water supply source connection portion 46 is connected to a water supply source 49 such as waterworks that supply water, through a hose or the like.

A dilution valve 47 is provided in a section of the water supply conduit 43 between the water filter 44 and the three-way valve 42. The dilution valve 47 is connected to the dilution conduit 48 that causes the dilution valve 47 and the disinfectant tank 20 to communicate with each other. The dilution valve 47 is switchable to a state of causing the water filter 44 and the three-way valve 42 to communicate with each other, or a state of causing the water filter 44 and the dilution conduit 48 to communicate with each other. The three-way valve 42, the water introduction valve 45, and the dilution valve 47 are connected to the control section 5, and operation of the valves are controlled by the control section 5.

When the three-way valve 42 is switched to the state of causing the circulation nozzle 14 and the treatment tank circulation conduit 40 to communicate with each other, the dilution valve 47 is switched to the state of the water filter 44 and the three-way valve 42 to communicate with each other, and operation of the liquid flow pump 41 is started while the liquid is stored in the treatment tank 2, the liquid inside the treatment tank 2 is discharged from the circulation nozzle 14 through the circulation port 13, the circulation conduit 13a, and the treatment tank circulation conduit 40.

In addition, when the three-way valve 42 is switched to the state of causing the circulation nozzle 14 and the water supply conduit 43 to communicate with each other, the dilution valve 47 is switched to the state of the water filter 44 and the three-way valve 42 to communicate with each other, and the water introduction valve 45 is opened, water supplied from the water supply source 49 is discharged from the circulation nozzle 14. The liquid discharged from the circulation nozzle 14 is introduced into the treatment tank 2.

Moreover, when the dilution valve 47 is switched to the state of causing the water filter 44 and the dilution conduit 48 to communicate with each other, and the water introduction valve 45 is opened, water supplied from the water supply source 49 is introduced into the disinfectant tank 20. Water may be supplied to the disinfectant tank 20 through the treatment tank 2 and the recovery conduit 23 without the dilution conduit 48.

Figure 2:
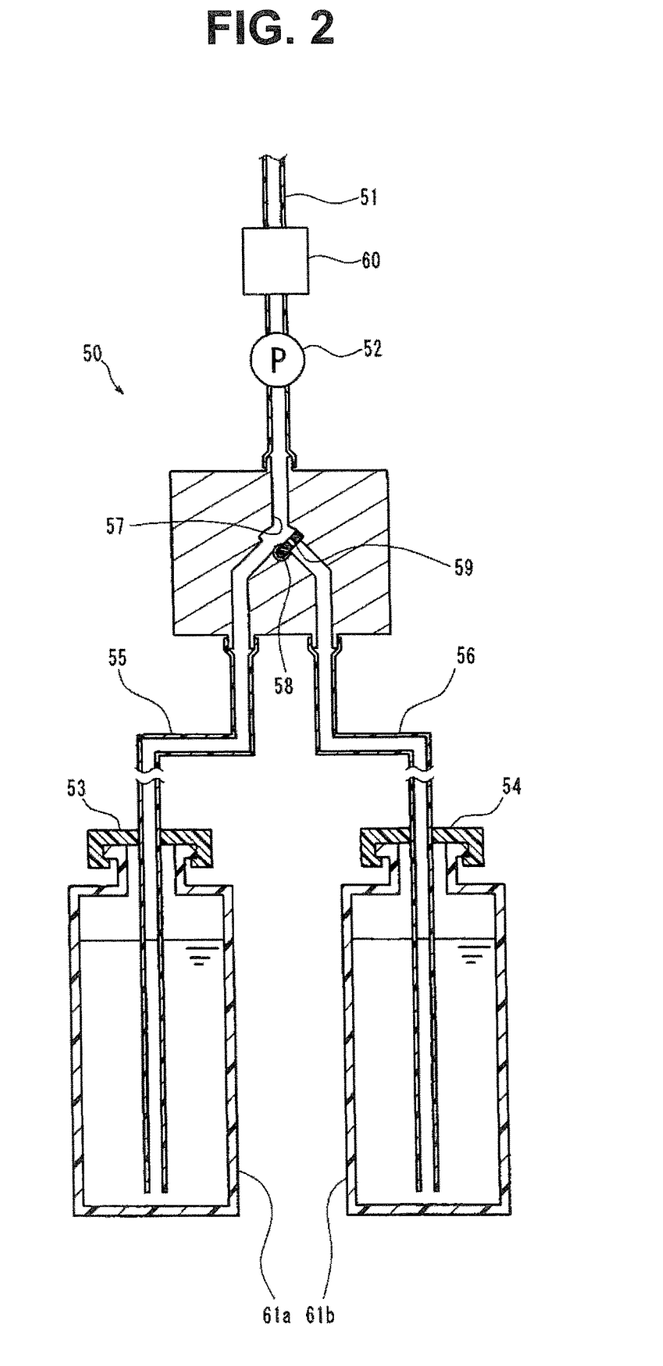
FIG. 2 is a diagram illustrating a configuration of the fluid feeding apparatus.

Next, detail of the configuration of the fluid feeding apparatus 50 is described. FIG. 2 is a diagram illustrating the configuration of the fluid feeding apparatus 50. The fluid feeding apparatus 50 includes the first connection portion 53, the second connection portion 54, a first flow path 55, a second flow path 56, a confluent part 57, the feed part 51, a suction portion 52, a resistance portion 59, and a switching portion 58.

The first connection portion 53 and the second connection portion 54 are respectively connected to the insides of the paired containers in which the liquid is stored. As mentioned above, the paired containers have no difference in the state of being not connected to the first connection portion 53 or the second connection portion 54. For the sake of description, a container connected to the first connection portion 53 is referred to as the first container 61a, and a container connected to the second connection portion 54 is referred to as the second container 61b.

The first connection portion 53 communicates with the first flow path 55. In addition, the second connection portion 54 communicates with the second flow path 56. The first flow path 55 and the second flow path 56 are joined at the confluent part 57. In other words, the confluent part 57 communicates with the inside of the first container 61a through the first flow path 55 and the first connection portion 53. In addition, the confluent part 57 communicates with the inside of the second container 61b through the second flow path 56 and the second connection portion 54.

The suction portion 52 is a suction pump connected to the confluent part 57 and the feed part 51. The suction portion 52 is operated to transfer the fluid from the confluent part 57 toward the feed part 51. Since the confluent part 57 communicates with the first connection portion 53 and the second connection portion 54 as mentioned above, the suction portion 52 is operated to suck the fluid from the first connection portion 53 and the second connection portion 54 at the same time, and feeds the fluid to the feed part 51.

The fluid that has been fed from the feed part 51 through operation of the suction portion 52 is introduced into the treatment tank 2 through the above-described fluid nozzle 15. In other words, the first flow path 55 and the second flow path 56 are connected to the treatment tank 2 through the suction portion 52.

The resistance portion 59 generates a difference of conduit resistance such that one of the first flow path 55 and the second flow path 56 is higher in conduit resistance than the other flow path and a flow rate of each of the first flow path 55 and the second flow path 56 exceeds zero during operation of the suction portion 52. The switching portion 58 is connected to the resistance portion 59, and switches a level relationship of the conduit resistance between the first flow path 55 and the second flow path 56 that is generated by the resistance portion 59. The switching portion 58 switches the level relationship of the conduit resistance between the first flow path 55 and the second flow path 56 in response to operation by the user of the endoscope reprocessor 1.

In other words, the fluid feeding apparatus 50 according to the present embodiment generates one of a state where the conduit resistance of the first flow path 55 is higher than the conduit resistance of the second flow path and a state where the conduit resistance of the first flow path 55 is lower than the conduit resistance of the second flow path, by the resistance portion 59 and the switching portion 58.

Accordingly, the fluid feeding apparatus 50 generates one of a state where the flow rate of the fluid sucked from the first container 61a through the first flow path 55 is larger than the flow rate of the fluid sucked from the second container 61b through the second flow path 56 and a state where the flow rate of the fluid sucked from the first container 61a through the first flow path 55 is smaller than the flow rate of the fluid sucked from the second container 61b through the second flow path 56, during the operation of the suction portion 52.

The configuration in which the resistance portion 59 and the switching portion 58 change the level relationship of the conduit resistance between the first flow path 55 and the second flow path 56 is not particularly limited. For example, the conduit resistance may be varied by varying a cross-sectional area of the flow path. Further, for example, the conduit resistance may be also varied by varying a length of the flow path or changing a bent shape of the flow path.

In the present embodiment, as an example, the resistance portion 59 and the switching portion 58 vary the cross-sectional area of each of the first flow path 55 and the second flow path 56 to change the level relationship of the conduit resistance between the first flow path 55 and the second flow path 56.

Figure 3:
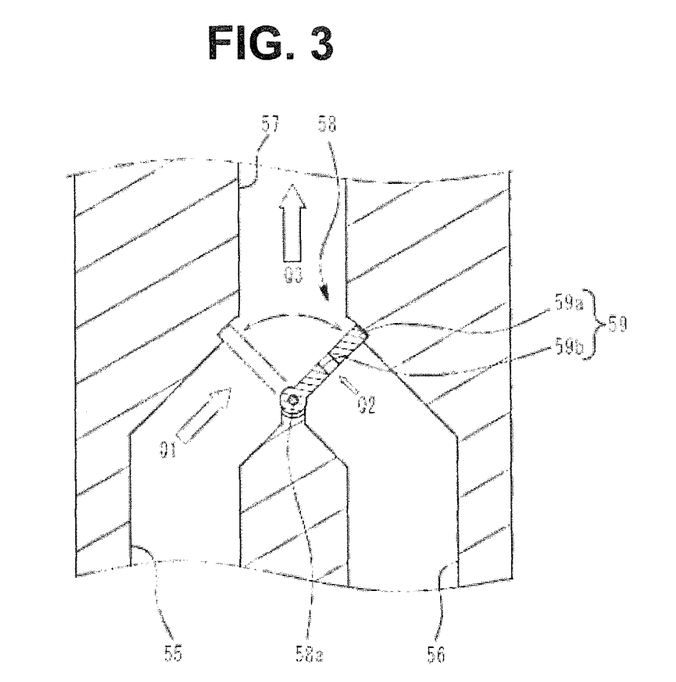
FIG. 3 is a cross-sectional diagram illustrating a configuration of a resistance portion and a switching portion.

FIG. 3 is a cross-sectional diagram illustrating the configuration of the resistance portion 59 and the switching portion 58. The resistance portion 59 according to the present embodiment has a valve part 59a that extends into one of the first flow path 55 and the second flow path 56 to make the cross-sectional area of the flow path in which the valve part 59a extends, smaller than the cross-sectional area of the other flow path. The valve part 59a is so configured as to make the cross-sectional area of the flow path in which the valve part 59a extends, smaller but as not to block the flow path. In the present embodiment, one or a plurality of opening parts 59b each serving as a through-hole are provided in the valve part 59a.

Figure 4:
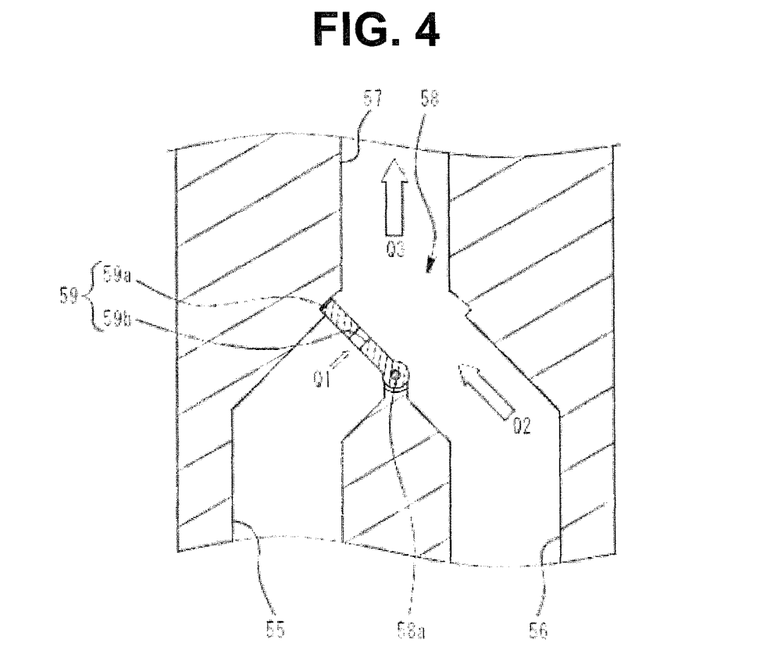
FIG. 4 is a cross-sectional diagram of the resistance portion and the switching portion, illustrating a state where a valve part extends into a first flow path.

The switching portion 58 movably supports the valve part 59a such that the valve part 59a is switchable to a state of extending into the second flow path 56 (a state illustrated in FIG. 3) and a state of extending into the first flow path 55 (a state illustrated in FIG. 4).

In the present embodiment, as an example, the switching portion 58 includes a supporting shaft part 58a at the position where the first flow path 55 and the second flow path 56 are joined. The supporting shaft part 58a pivotally supports the valve part 59a. The valve part 59a pivots about the supporting shaft part 58a to move between a state of being located in an opening part of the first flow path 55 that opens at the confluent part 57 and a state of being located in an opening part of the second flow path 56 that opens at the confluent part 57.

In the state where the valve part 59a extends into the second flow path 56, the conduit resistance of the first flow path 55 becomes lower than the conduit resistance of the second flow path 56. In addition, in the state where the valve part 59a extends into the first flow path 55, the conduit resistance of the first flow path 55 becomes higher than the conduit resistance of the second flow path 56.

In the following description, the flow rate of the first flow path 55 is denoted by Q1, and the flow rate of the second flow path 56 is denoted by Q2 under the condition that the suction portion 52 is operated to suck the fluid at a flow rate Q3. The flow rate Q3 of the suction portion 52 indicates a flow rate of the fluid that is fed from the feed part 51 by the fluid feeding apparatus 50. Further, the flow rate Q3 is a total of the flow rate Q1 and the flow rate Q2, and each of the flow rate Q1 and the flow rate Q2 exceeds zero.

In the state where the valve part 59a extends into the second flow path 56, the flow rate Q1 becomes higher than the flow rate Q2 in the case where the suction portion 52 is operated to suck the fluid at the flow rate Q3. On the other hand, in the state where the valve part 59a extends into the first flow path 55, the flow rate Q1 becomes smaller than the flow rate Q2 in the case where the suction portion 52 is operated to suck the fluid at the flow rate Q3.

In addition, in the present embodiment, as an example, the conduit resistance of the first flow path 55 in the state where the valve part 59a does not extend into the first flow path 55 is substantially equal to the conduit resistance of the second flow path 56 in the state where the valve part 59a does not extend into the second flow path 56.

Therefore, when the resistance portion 59 and the switching portion 58 change the level relationship of the conduit resistance between the first flow path 55 and the second flow path 56, the ratio of the flow rate Q1 and the flow rate Q2 to the flow rate Q3 is simply inverted. More specifically, when the ratio of the flow rate Q1 and the flow rate Q2 to the flow rate Q3 is assumed to be X:1 (here, X>1) in the state where the valve part 59a extends into the second flow path 56, the ratio of the flow rate Q1 and the flow rate Q2 in the state where the valve part 59a extends into the first flow path 55 becomes 1:X.

Note that the conduit resistance of the first flow path 55 in the state where the valve part 59a does not extend into the first flow path 55 may be different from the conduit resistance of the second flow path 56 in the state where the valve part 59a does not extend into the second flow path 56.

Moreover, in the present embodiment, as an example, the fluid feeding apparatus 50 includes a flow rate detection section 60 that measures the flow rate of the fluid fed from the feed part 51. The fluid feeding apparatus 50 calculates a volume of the fluid fed from the feed part 51, on the basis of the detection result of the flow rate detection section 60.

Note that, when the endoscope reprocessor 1 includes a flow rate detection section that measures the flow rate of the fluid fed from the feed part 51, the fluid feeding apparatus 50 may not include the flow rate detection section 60. In this case, the control section 5 of the endoscope reprocessor 1 calculates the volume of the fluid fed from the fluid feeding apparatus 50, on the basis of the detection result of the flow rate detection section, and controls the operation of the fluid feeding apparatus 50 to feed a predetermined volume of the fluid.

As described above, the fluid feeding apparatus 50 sucks the fluid from the first container 61a and the second container 61b that are respectively connected to the first connection portion 53 and the second connection portion 54, and feeds the predetermined volume of the fluid from the feed part 51.

Further, when the valve part 59a of the resistance portion 59 is moved by the switching portion 58 to feed the predetermined volume of fluid, it is possible for the fluid feeding apparatus 50 to switch the states between the state where the volume of the fluid sucked from the first container 61a becomes larger than the volume of the fluid sucked from the second container 61b and the state where the volume of the fluid sucked from the first container 61a becomes smaller than the volume of the fluid sucked from the second container 61b.

Figure 5:
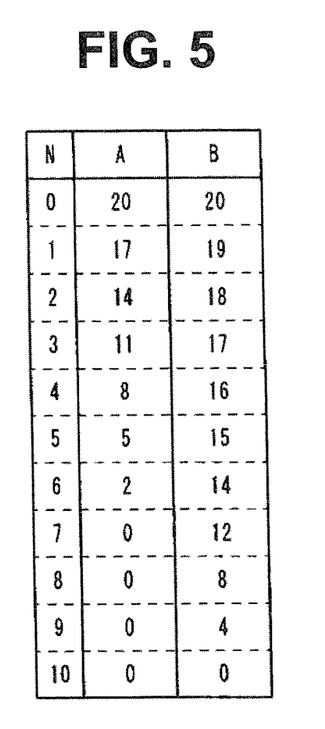
FIG. 5 is a table to explain action of the fluid feeding apparatus.
Figure 6:
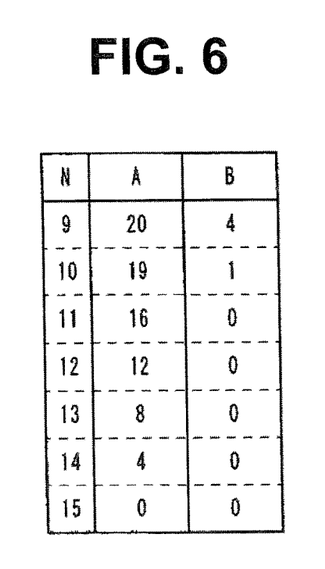
FIG. 6 is a table to explain the action of the fluid feeding apparatus.
Figure 7:
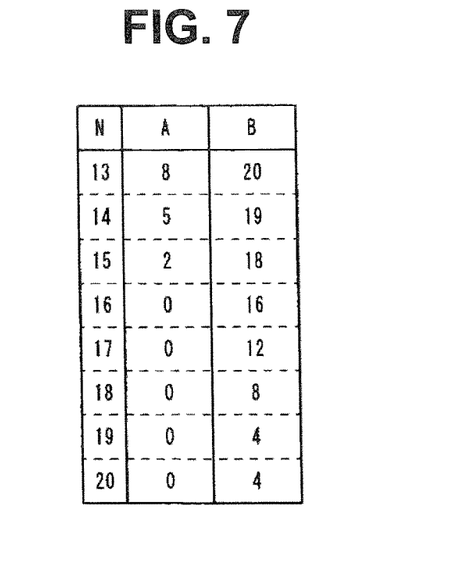
FIG. 7 is a table to explain the action of the fluid feeding apparatus.

Action and effects of the fluid feeding apparatus 50 having the above-described configuration are described. FIG. 5 to FIG. 7 are tables to explain the action of the fluid feeding apparatus 50.

In the following, as an example, the fluid feeding apparatus 50 switches the ratio of the flow rate Q1 of the first flow path 55 and the flow rate Q2 of the second flow path 56 to the flow rate Q3 of the fluid fed from the feed part 51, between 3:1 and 1:3, by the resistance portion 59 and the switching portion 58. Further, an unused container stores the fluid of a volume of five times the volume of the fluid fed per one feeding operation by the fluid feeding apparatus 50. Since two containers of the first container 61a and the second container 61b are connectable to the fluid feeding apparatus 50, it is possible for the fluid feeding apparatus 50 to perform the fluid feeding operation ten times successively when the first container 61a and the second container 61b that are both unused are connected to the fluid feeding apparatus 50 in the present embodiment.

In the table illustrated in FIG. 5, the number of executions of the feeding operation after the unused first container 61a and the unused second container 61b are connected to the fluid feeding apparatus 50 is denoted by N. In addition, a column A indicates a residual amount of the fluid stored in the first container 61a after completion of the N-th fluid feeding operation. Likewise, a column B indicates a residual amount of the fluid stored in the second container 61b after completion of the N-th fluid feeding operation.

In the example illustrated as the table of FIG. 5, 20 volumes (unit is undefined) of the liquid is stored in the unused first container 61a and the unused second container 61b, and the fluid feeding apparatus 50 feeds 4 volumes of the fluid per one feeding operation. Further, in the example illustrated in FIG. 5, the valve part 59a extends into the second flow path 56, and the ratio of the flow rate Q1 of the first flow path 55 and the flow rate Q2 of the second flow path 56 to the flow rate Q3 of the fluid fed from the feed part 51 is 3:1.

As illustrated in FIG. 5, both of the first container 61a and the second container 61b become empty after the fluid feeding apparatus 50 completes the tenth fluid feeding operation. Further, the first container 61a that communicates with the first flow path 55 having the conduit resistance lower than the conduit resistance of the second flow path 56, becomes empty prior to the second container 61b. In the present example, 3 volumes of the liquid has been sucked from the first container 61a and 1 volume of the liquid has been sucked from the second container 61b at the time when the first fluid feeding operation is completed.

Accordingly, the first container 61a becomes empty at the time when the sixth fluid feeding operation is completed, and the fluid is sucked only from the second container 61b in the seventh to tenth feeding operation.

As mentioned above, in the fluid feeding apparatus 50 of the present embodiment, the flow rate Q1 of the first flow path 55 and the flow rate Q2 of the second flow path 56 to the flow rate Q3 of the fluid fed from the feed part 51 are made different from each other, and the fluid stored in one of the paired containers (61a and 61b) respectively connected to the first flow path 55 and the second flow path 56 is accordingly consumed prior to the fluid stored in the other container. Further, the fluid is sucked from the other container after the one container becomes empty, which allows the fluid feeding apparatus 50 to perform the fluid feeding operation until the other container becomes empty. Accordingly, if the one container is replaced with an unused container by the user during a period from the time when the one container becomes empty to the time when the other container becomes empty, it is possible for the fluid feeding apparatus 50 to repeatedly perform the fluid feeding operation continuously.

In the example illustrated in FIG. 5, if the first container 61a is replaced with a new unused container by the user during a period from completion of the sixth fluid feeding operation to completion of the tenth fluid feeding operation, a time period in which the fluid feeding apparatus 50 cannot suck the fluid from the container and suspends the operation due to incompletion of the feeding operation, does not occur.

FIG. 6 illustrates a case where the first container 61a is replaced with a new unused container by the user at the time when the ninth fluid feeding operation is completed in the example illustrated in FIG. 5. In this case, the residual amount of the first container 61a before execution of the tenth fluid feeding operation is 20 volumes, and the residual amount of the second container 61b is 4 volumes.

In addition, the user operates the switching portion 58 to cause the valve part 59a of the resistance portion 59 to extend into the first flow path 55. Accordingly, in the example illustrated in FIG. 6, the ratio of the flow rate Q1 of the first flow path 55 and the flow rate Q2 of the second flow path 56 to the flow rate Q3 of the fluid fed from the feed part 51 becomes 1:3.

In the example illustrated in FIG. 6, the second container 61b that communicates with the second flow path 56 having the conduit resistance lower than the conduit resistance of the first flow path 55 becomes empty prior to the first container 61a. In the example illustrated in FIG. 6, although it is possible to complete the 15-th fluid feeding operation due to replacement of the first container 61a, the second container 61b becomes empty at the time when the tenth fluid feeding operation is completed.

Therefore, in the example illustrated in FIG. 6, if the second container 61b is replaced with a new unused container by the user during a period from completion of the tenth fluid feeding operation to completion of the 15-th fluid feeding operation, a time period in which the fluid feeding apparatus 50 cannot suck the fluid from the container and suspends the operation due to incompletion of the feeding operation, does not occur.

FIG. 7 illustrates a case where the second container 61b is replaced with a new unused container by the user at the time when the 13-th fluid feeding operation is completed in the example illustrated in FIG. 6. In this case, the residual amount of the first container 61a before the execution of the 14-th fluid feeding operation is 8 volumes, and the residual amount of the second container 61b is 20 volumes.

In addition, the user operates the switching portion 58 to cause the valve part 59a of the resistance portion 59 to extend into the second flow path 56. Accordingly, in the example illustrated in FIG. 7, the ratio of the flow rate Q1 of the first flow path 55 and the flow rate Q2 of the second flow path 56 to the flow rate Q3 of the fluid fed from the feed part 51 becomes 3:1.

In the example illustrated in FIG. 7, the first container 61a that communicates with the first flow path 55 having the conduit resistance lower than the conduit resistance of the second flow path 56 becomes empty prior to the second container 61b. In the example illustrated in FIG. 7, although it is possible to complete the 20-th fluid feeding operation due to replacement of the second container 61b, the first container 61a becomes empty at the time when the 15-th fluid feeding operation is completed.

Therefore, in the example illustrated in FIG. 7, if the first container 61a is replaced with a new unused container by the user during a period from completion of the 15-th fluid feeding operation to completion of the 20-th fluid feeding operation, a time period in which the fluid feeding apparatus 50 cannot suck the fluid from the container and suspends the operation due to incompleteness of the feeding operation, does not occur.

As described above with reference to the tables of FIG. 5 to FIG. 7, in the fluid feeding apparatus 50 of the present embodiment, the fluid stored in one of the paired connected first container 61a and connected second container 61b is consumed prior to the fluid stored in the other container, which makes it possible to create the time period allowing for replacement of the empty container without stopping repetitive execution of the feeding operation in the case where the feeding operation of the fluid from the feed part 51 is repeated.

Accordingly, even if it is not possible for the user to replace the one container immediately after the one container becomes empty, it is possible for the fluid feeding apparatus 50 to continuously perform the fluid feeding operation when the user replaces the one container before the other container becomes empty. Therefore, the fluid feeding apparatus 50 of the present embodiment makes it possible to prevent occurrence of the time period in which the feeding operation is suspended due to shortage of the fluid in the container. Moreover, the endoscope reprocessor 1 including such a fluid feeding apparatus 50 makes it possible to prevent occurrence of a time period in which the reprocessing is suspended due to shortage of the fluid in the container.

Note that, in the present embodiment described above, the resistance portion 59 and the switching portion 58 of the fluid feeding apparatus 50 have the configuration in which the valve part 59a including the one or the plurality of opening parts 59b is pivoted to extend into one of the first flow path 55 and the second flow path 56; however, the configuration of the resistance portion 59 and the switching portion 58 is not limited to the configuration of the present embodiment.

Figure 8:
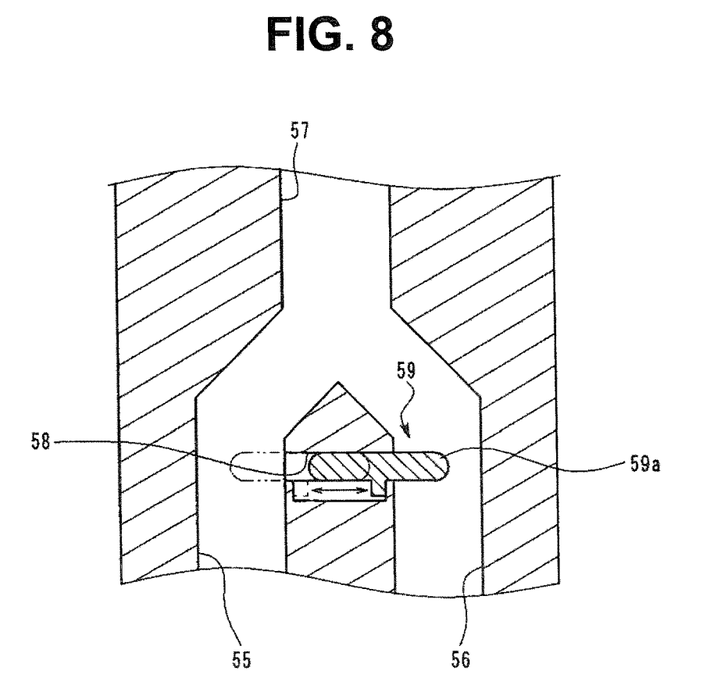
FIG. 8 is a cross-sectional diagram illustrating a first modification of the resistance portion and the switching portion.

FIG. 8 is a cross-sectional diagram illustrating a first modification of the resistance portion 59 and the switching portion 58. In the first modification illustrated in FIG. 8, the valve part 59a of the resistance portion 59 is a plate-like or columnar member that extends into one of the first flow path 55 and the second flow path 56.

The valve part 59a extends into the first flow path 55 or the second flow path 56, thereby decreasing the cross-sectional area of the flow path without blocking the flow path. The valve part 59a is supported by the switching portion 58, and linearly moves between a position projecting from a side wall surface of the first flow path 55 to the inside of the first flow path 55 and a position projecting from a side wall surface of the second flow path 56 to the inside of the second flow path 56.

Figure 9:
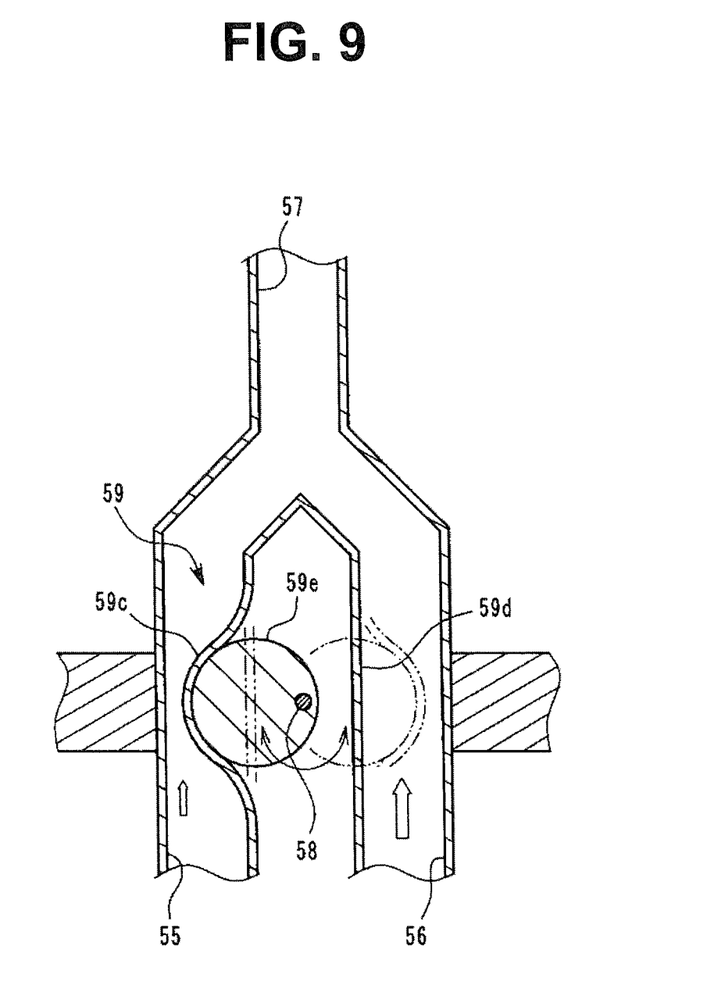
FIG. 9 is a cross-sectional diagram illustrating a second modification of the resistance portion and the switching portion.

FIG. 9 is a cross-sectional diagram illustrating a second modification of the resistance portion 59 and the switching portion 58. In the second modification illustrated in FIG. 9, the resistance portion 59 includes deformation parts 59c and 59d each made of a flexible material, and a pressing part 59e. The deformation parts 59c and 59d are respectively provided on the side wall surfaces of the first flow path 55 and the second flow path 56. The pressing part 59e presses one of the deformation parts 59c and 59d from the outside toward the inside of the first flow path 55 and the second flow path 56. The pressing part 59e is supported by the switching portion 58, and is moved between a position at which the pressing part 59e presses the deformation part 59c from the outside toward the inside of the first flow path 55 and a position at which the pressing part 59e presses the deformation part 59c from the outside toward the inside of the second flow path 56.

In the present modification, one of the deformation parts 59c and 59d protrudes in one of the flow paths by being pressed by the pressing part 59e, which makes the cross-surface area of the one of the first flow path 55 and the second flow path 56 smaller than the cross-sectional area of the other flow path.

The resistance portions 59 and the switching portions 58 according to the first and second modifications described above also make it possible to generate the difference of the conduit resistance such that one of the first flow path 55 and the second flow path 56 is higher in conduit resistance than the other flow path and the flow rate of each of the first flow path 55 and the second flow path 56 exceeds zero during the operation of the suction portion 52 and to switch the level relationship of the conduit resistance between the first flow path 55 and the second flow path 56.

The present invention is not limited to the above-described embodiment, and the present invention may be appropriately modified without departing from the essence or spirit of the invention that can be read from the claims and the entire specification, and a fluid feeding apparatus and an endoscope reprocessor which involve such modifications are also intended to be within the technical scope of the present invention.

What is claimed is:

1. A fluid feeding apparatus, comprising:
   a first connector configured to be connected to a first container in which fluid is stored;
   a second connector configured to be connected to a second container in which fluid is stored;
   a first flow path that communicates with the first connection portion;
   a second flow path that communicates with the second connection portion;
   a confluent part at which the first flow path and the second flow path are joined;
   a suction pump connected to a feed part and the confluent part, the suction pump being configured to suck the fluid from the first connection portion and the second connection portion at the same time to feed the fluid to the feed part;
   a valve that selectively extends into one of the first flow path and the second flow path;

one or more through-holes formed in the valve, and configured to penetrate through the valve in one of the first and second flow paths into which the valve extends; and a switching portion configured to movably support the valve between a position at which the valve extends into the first flow path and a position at which the valve extends into the second flow path, wherein fluid, which flows through one of the first and second flow paths into which the valve extends, reaches the confluent part through the one or more through-holes, during operation of the suction pump.

2. An endoscope reprocessor, comprising:

a treatment tank in which an endoscope is disposed; and the fluid feeding apparatus according to claim 1, wherein the first flow path and the second flow path are connected to the treatment tank through the suction pump.

3. The fluid feeding apparatus according to claim 1, wherein the switching portion includes a supporting shaft configured to support the valve such that the valve pivots in the confluent part.

\* \* \* \* \*